United States Patent [19]

Burzynski et al.

[11] Patent Number: 5,686,648
[45] Date of Patent: Nov. 11, 1997

[54] CONTINUOUS PROCESS FOR THE ISOMERIZATION OF OLEFINS WITH REGENERATION OF THE CATALYST

[75] Inventors: Jean-Pierre Burzynski, Sainte-Foy-Les Lyon; Christine Travers, Rueil Malmaison; Didier Duee, Eragny sur Oise; Larry Mank, Orgeval; Jean De Bonneville, Bougival, all of France

[73] Assignee: Institut Francais du Petrole, Rueil Malmaison, France

[21] Appl. No.: 487,091

[22] Filed: Jun. 6, 1995

Related U.S. Application Data

[63] Continuation of Ser. No. 195,010, Feb. 9, 1994, abandoned.

[30] Foreign Application Priority Data

Feb. 9, 1993 [FR] France .................. 93 01389

[51] Int. Cl.$^6$ .................. C07C 5/22; C07C 5/27
[52] U.S. Cl. .................. 585/671; 502/38; 502/41; 502/55
[58] Field of Search .................. 585/671; 502/38, 502/41, 55

[56] References Cited

U.S. PATENT DOCUMENTS

| | | | |
|---|---|---|---|
| 3,558,733 | 1/1971 | Myers | 260/683.2 |
| 4,225,419 | 9/1980 | Myers | 208/135 |
| 4,367,362 | 1/1983 | Franz et al. | 585/671 |
| 5,182,247 | 1/1993 | Kuhlmann et al. | 585/671 |
| 5,321,195 | 6/1994 | Travers et al. | 585/671 |

*Primary Examiner*—Glenn A. Caldarola
*Assistant Examiner*—Elizabeth D. Wood
*Attorney, Agent, or Firm*—Millen, White, Zelano & Branigan, P.C.

[57] ABSTRACT

Continuous process for the skeletal isomerization of n-olefins containing at the most 20 carbon atoms, in the presence of a catalyst essentially constituted by alumina and titanium, in which a charge containing the said n-olefins is made to flow through at least one fluidized bed reaction zone, the catalyst flowing into each reaction zone. The catalyst drawn off from the final reaction zone is passed into a regeneration zone, at the outlet of which it is passed into a zone where it undergoes a steam treatment prior to its reintroduction into the first reaction zone. The process is performed in the presence of steam, so that the catalyst is in contact with 3 to 85 wt. % (based on the catalyst weight) of steam. The water/olefin charge molar ratio in the reaction zone is between 0.1 and 3.

9 Claims, 1 Drawing Sheet

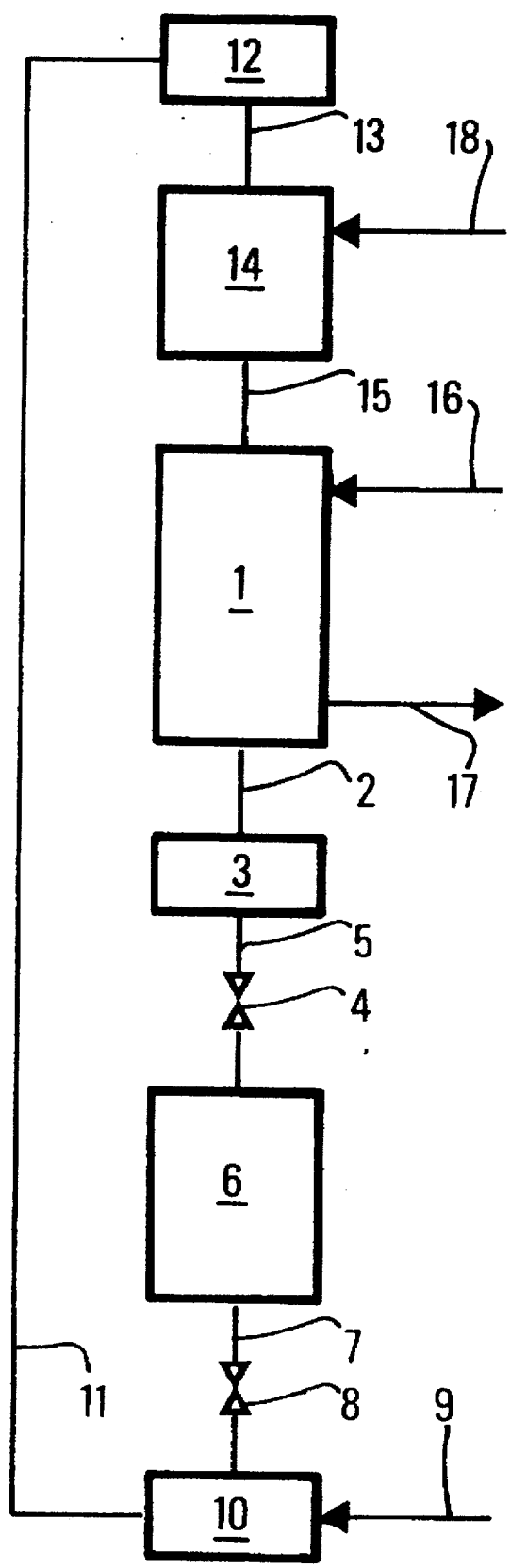

CONTINUOUS PROCESS FOR THE ISOMERIZATION OF OLEFINS WITH REGENERATION OF THE CATALYST

This application is a continuation of application Ser. No. 08/195,010 filed Feb. 29, 1994 and now abandoned.

The present invention relates to a continuous process for skeletal isomerization with regeneration of the alumina and titanium-based catalyst.

BACKGROUND OF THE INVENTION

The reduction of lead alkyls in petrol has led the refiner to consider the incorporation into the petrol of various compounds and in particular alcohols and ethers, so as to make it possible to increase the octane number. Apart from methanol, which is one of the most interesting known additives, MTBE (methyl tert. butyl ether) and TAME (tert. amyl methyl ether) have antiknock properties making it possible to improve the quality of the petrol and increase the octane number thereof, the increase exceeding that obtained with methanol. These two additives also have numerous other advantages such as:

a boiling point corresponding to that of components of the petrol having the lowest antiknock properties,
a vapor pressure compatible with the above components,
an excellent freezing point,
a limited solubility in water,
a complete miscibility with hydrocarbons.

MTBE is generally obtained from isobutene and methanol. TAME is obtained from isoamylenes and methanol. The isobutene and isopentenes used are generally contained in $C_3$—$C_4$—$C_5$ olefin fractions resulting from the effluents of catalytic cracking and steam cracking. However, the quantities of isobutene and isopentenes supplied by these different processes are not adequate to permit a wide scale development of MTBE and TAME production processes.

Therefore, with a view to producing large quantities of isobutene and isopentenes, it has been proposed to completely or almost completely isomerize into isobutene and isopentenes, the butenes and pentenes contained in the effluents of the aforementioned processes.

Numerous processes associated with numerous catalysts have been developed, e.g., processes using alumina-based catalysts or more particularly aluminas activated or treated with vapor, halogen-containing aluminas, bauxite or alumina treated with boron, and silicon or zirconium derivatives. Thus, e.g. U.S. Pat. No. 3,558,744 describes a skeletal isomerization process using an (eta or gamma) alumina catalyst or a halogen or boron-containing alumina catalyst at 315° to 595° C. When the activity of the catalyst has reduced to an unacceptable value, the olefin charge supply is interrupted and the catalyst regenerated. It is calcined at approximately 600° C. (480° to 650° C.) in the presence of oxygen and then cooled to 315° to 480° C. before treatment with steam. The water quantity added for this treatment is such that the water content of the catalyst is between 0.75 and 2.5%. This catalyst is then recontacted with the charge in the presence of water (5 to 100 ppm), so as to maintain a water quantity of 0.75 to 2.5% in contact with the catalyst.

EP-32,543 describes a skeletal isomerization process using a fluorine-containing alumina catalyst. After regeneration in the presence of steam, this catalyst requires a supplemental treatment with a fuorine-containing compound, in order to maintain the fluorine content on the catalyst. The isomerization reaction takes place with enormous quantities of water (30 to 400 mole %).

Most of these processes have a relatively low conversion per pass and a limited selectivity due to parasitic reactions such as cracking and polymerization. This leads to a reduction in the performance characteristics in time, which leads to frequent regenerations of the catalyst and consequently to a discontinuous operation of the installations, the reactor not operating when the catalyst is being regenerated. Moreover, processes using fluorine-containing alumina require a fluorine-containing compound supply, which makes operation more complicated.

SUMMARY OF THE INVENTION

The present invention aims at obviating these disadvantages by using a simple, continuously operating process, which makes it possible to increase the production of the installation and the life of the equipment, by reducing thermal stresses, while at the same time reducing costs as a result of reduced equipment size.

In an original manner, this process uses a catalyst based on alumina and titanium (0.03 to 0.6%) which, in contact with a given steam quantity (3 to 85 wt. %, based on the catalyst weight) is particularly suitable for a continuous process with integrated regeneration.

More specifically, the invention relates to a process for the skeletal isomerization of n-olefins containing at the most 20 carbon atoms, in which the charge containing the n-olefins is, in a reaction zone, contacted with an alumina-based catalyst in the presence of water and the spent catalyst is regenerated and then treated with steam before being recontacted with the charge, the temperature in the reaction zone being between 300° and 600° C., the pressure between 1 and 10 bar and the space velocity of the charge between 0.1 and 10 $h^{-1}$. This continuous process operates with a circulation of catalyst containing alumina and 0.03 to 0.6% titanium (by weight), the catalyst passing through the reaction zone being drawn off for regeneration and treatment with steam at a temperature substantially equal to that of the reaction zone and the steam quantity in contact with the catalyst in the reaction zone and during the treatment after regeneration is between 3 and 85 wt. % based on the catalyst weight, the water quantity introduced into the reaction zone also being in a water/olefin charge molar ratio between 0.1 and 3.

More specifically the present invention relates to the production of isoolefins on the basis of a charge containing n-olefins usually having 4 to 6 carbon atoms. It more particularly relates to the isomerization of n-butenes into isobutenes and n-pentenes into isopentenes (isoamylenes). The process comprises means for the injection of steam after regeneration, because this surprisingly leads to an improvement in the performance characteristics and the stability of the catalyst, as well as in its life.

The charge flows through at least one catalytic zone, which is usually vertical. This catalytic zone is usually constituted by a bed (or several beds) having a radial flow direction. It is, e.g., identical to that described in U.S. Pat. No. 4,277,444. Throughout the present text the term reaction zone will be used to cover all the reaction zones, no matter whether there is one or several such zones.

In this vertical zone the catalyst is generally in a slow downward movement and is continuously or periodically extracted from the final catalytic zone and is then passed into a regeneration zone at the outlet of which the regenerated catalyst is returned to the head of the first catalytic zone in order to maintain a substantially constant activity in each of the zones.

An appropriate frequency and level are adopted for the drawing off of the catalyst from the final catalytic zone. For example, the catalyst can be drawn off either continuously, or periodically, e.g. at a frequency of 1/10 to 10 days, while only drawing off at the same time a fraction e.g. 0.5 to 15% of the total catalyst quantity.

It is also possible to draw off this catalyst with a much faster frequency of approximately one minute or one second, the proportion of the quantity drawn off then being reduced.

In general terms, in the continuous process according to the invention, the catalyst can flow continuously between the reaction zone, the regeneration, the steam treatment and the reaction zone again. At certain times the flow can also take place periodically, but at a relatively high frequency, as has e.g. been described for the drawing off of the catalyst from the reaction zone. The catalyst flow is adapted so as to maintain a quasi-constant catalyst activity in the reactor.

To this end, the apparatus can incorporate means for the periodic transfer of the catalyst between the reaction zone and the regeneration reactor and/or between the regeneration reactor and the steam treatment zone and/or between the regeneration reactor and the reaction zone and/or between the steam treatment zone and the reaction zone.

The spent or partly spent catalyst from the final catalytic zone is then passed by gravity to a "storage" balloon flask positioned below the final catalytic zone and above the regeneration zone.

The catalyst can be regenerated batchwise or continuously using any known means. With the batchwise procedure the spent or partly spent catalyst is stored in the "storage" flask before supplying the generator generally positioned below said flask. At regular intervals the regenerator is brought into pressure equilibrium e.g. under a steam or nitrogen atmosphere with the "settling/storage" flask. It is then filled with catalyst passing from said flask through a system of valves and is then isolated from the remainder of the system. The regenerator is then purged with nitrogen or steam in order to eliminate the hydrocarbons and catalyst regeneration takes place. The regenerator or storage balloon flask into which has been transferred the regenerated catalyst, is then purged with nitrogen or steam and then placed under steam in pressure equilibrium with the catalytic zone into which the catalyst is to be injected.

The actual regeneration of the catalyst is performed by combustion of coke deposits. This operation takes place by injecting a mixture containing air diluted by steam or nitrogen. The oxygen content of the regeneration gas injected at the head of the regenerator is preferably between 0.01 and 2 vol. %. The oxygen of the injected gaseous mixture is consumed by the combustion of the coke deposits end the end of combustion is easily detected by an increase in the oxygen content in the gas passing out of the regenerator and also by the disappearance of the flame front (horizontal plane where combustion occurs), which propagates from the top to bottom of the catalytic bed. Combustion takes place at an average temperature preferably between 350° and 550° C. and under a pressure which is e.g. between 1 and 15 bars. This treatment can last between 20 minutes and 3 hours and generally lasts about one hour. In the process according to the invention, it is particularly indicated to regenerate at a temperature substantially equal to (±40° C. and even better ±20° C.) that prevailing in the reaction zone.

The catalyst then undergoes a steam treatment normally at between 110° and 700° C. and in preferred manner between 200° and 600° C. and even more advantageously at a temperature substantially equal to (±40° C. and still better ±20° C.) that prevailing in the reaction zone, under a partial steam pressure exceeding 0.1 bar and preferably between 0.6 and 4 bars for between 6 minutes and 10 hours and preferably 30 minutes and 3 hours.

This treatment makes it possible to maximize the proportion of Bronsted sites on the alumina/titanium catalyst when the steam quantity in contact with the catalyst is between 3 and 85 wt. % (based on the catalyst weight) and preferably 10 to 60 and even more advantageously 10 to 40 or 18 to 35%.

The regenerated catalyst is then raised by a gas lift to a "storage/settling" balloon flask positioned above the reactor. The lift fluid used for conveying the catalyst can be any random inert fluid and is very advantageously steam.

In the storage/settling flask the steam is separated from the catalyst and passed to a filter in order to eliminate the fine catalyst particles and from there is passed to a compressor with a view to its recycling to the reaction zone, to the lifts or to the regeneration zone.

According to a variant of the process the steam treatment zone can be positioned downstream of the storage/settling flask and upstream of the first catalytic zone.

The fresh and/or regenerated catalyst progressively supplies, as the spent catalyst is drawn off, the chosen reaction zone or the steam treatment zone, in order to maintain a quasi-constant activity in the reactor.

The charge to be isomerized is contacted with the catalyst at a temperature between 300° and 600° C. (and preferably between 400° and 550° C. when it is constituted by butenes and/or pentenes) at a pressure between 1 and 10 bars absolute (and preferably between 1 and 5 bars absolute when the charge is constituted by n-butenes and/or n-pentenes.

The space velocity is between 0.1 and 10 $h^{-1}$ expressed by volume of olefin charge per volume of catalyst and per hour (and in preferred manner between 0.5 and 6 $h^{-1}$ when the charge is constituted by butenes and/or pentenes).

According to the invention, the process is performed in the presence of water in order to minimize undesirable secondary reactions. The water quantity introduced into the reactor is such that the water/olefin charge molar ratio is between 0.1 and 3 and preferably between 0.3 and 2 and even more advantageously between 0.5 and 2, e.g. when the charge is constituted by n-butenes and/or n-pentenes. This supply of water makes it possible to maintain the steam quantity in contact with the catalyst at 10 to 40% by weight (based on the catalyst weight) in order to maintain the performance characteristics of the catalyst.

The catalyst used in the present invention is a catalyst containing (apart from the optionally fixed water) alumina and 0.03 to 0.6 wt. % titanium. The catalyst is preferably in granular form.

The catalyst grains are usually in the form of substantially spherical balls with a diameter generally between 1 and 3 mm and preferably between 1.5 and 2 mm. The specific surface of the support is usually between 10 and 500 $m^2/g$ and preferably between 50 and 450 $m^2/g$, its pore volume being between 0.4 and 0.8 $cm^3/g$.

The new catalyst is preferably treated before use under steam and before being contacted with hydrocarbons, said treatment taking place at between 110° and 700° C. under a partial steam pressure exceeding 0.1 bar for between 0.1 and 120 hours.

The invention also relates to an apparatus for the isomerization of n-olefins containing at the most 20 carbon atoms, said apparatus comprising at least one isomerization reactor (1) containing an alumina-based catalyst, provided with a pipe (15) for the introduction of the catalyst, a pipe (2) for its extraction, a pipe (16) for the introduction of the charge containing the n-olefins and a pipe (17) for the extraction of the treated charge; a regenerator (6) equipped with a pipe (5) for the introduction of the spent catalyst and a pipe (7) for the extraction of the regenerated catalyst, means for the introduction of the regeneration gas and for the discharge of the gases formed; a pneumatic lift (10, 11) with a motor gas supply pipe (9) and passing into a storage/settling balloon flask (12).

Advantageously, the regenerator is provided with a steam introduction pipe. Between the isomerization reactor and the storage/settling flask (12) is advantageously located a reactor (14) for the treatment of the steam of the regenerated catalyst introduced by the pipe (13), said reactor having a pipe (15) for the transfer of the treated catalyst to the isomerization reactor.

This apparatus can have means for the periodic transfer of the catalyst between the reactor (1) and the regenerator (6). It also has either means for the periodic transfer of the catalyst between the regenerator (6) and the reactor (1), all means for the periodic transfer of the catalyst between the reactors (14) and (1).

FIG. 1 diagrammatically illustrates the invention without limiting its scope. In the construction diagrammatically illustrated in FIG. 1 a single reaction zone is shown in which the catalyst flows from top to bottom.

The charge enters at the top of the reactor (1) and passes out at the bottom. The new catalyst is introduced by the pipe (15) at the top of the reactor (1) and the spent catalyst is drawn off by the pipe (2) and is directed through the storage flask (3) and the line (5) to the regeneration zone (6). The regenerator is brought into pressure equilibrium with the reactor under a nitrogen or steam atmosphere. The regenerator is then isolated from the remainder of the system by closing the valves (4) and (8) and the combustion of the coke described hereinbefore is performed in fixed or fluidized bed.

In a first variant of the process said stage is followed by the aforementioned vapor treatment. When this treatment is finished, the regenerator is placed under pressure equilibrium with the reactor. The catalyst is passed by the line (7) to a buffer flask (12), is raised by a pneumatic lift (11), operating with a motor gas introduced by the line (9) and which is preferably steam and passed to the storage/settling flask (12). The catalyst which is regenerated and pretreated with steam is directly introduced by the line (13, 15) into the reactor (1).

In a second variant of the process only the coke combustion stage is performed in the regenerator (6). The coke-free catalyst is passed by the line (7) to the buffer flask (10), raised by a lift (11), operating with the motor gas introduced by the line (9), which is steam or nitrogen end supplied to the storage/settling flask (12) and then by the line (13) to a zone or reactor (14), where it is vapor treated under the conditions described hereinbefore. The catalyst which has been regenerated and pretreated with steam is progressively introduced into the reactor (1) by the line (15).

The continuous process according to the invention leads to significant productivity gains, an extended equipment life and also to reduced capital expenditure as a result of the reduced size of the equipment compared with a batch process. The latter advantage is particularly significant with respect to the vapour treatment, which here requires smaller vapour quantities as a result of the lower regenerated quantities per pass.

The invention is particularly advantageous when an alumina/titanium catalyst is used, the coking level of said catalyst being reduced and the use of the continuous regeneration circuit permits an operation of the reactors at a high activity level and the maintaining of this level over a long period of time.

The following examples illustrate the invention without limiting its scope.

The isomerization performance characteristics are expressed by 1) the conversion of butenes $$C = \frac{\Sigma(\% \; n\text{-butenes}) \; \text{charge} - \Sigma(\% \; n\text{-butenes}) \; \text{effluent}}{\Sigma(\% \; n\text{-butenes}) \; \text{charge}} \times 100$$

2) the isobutene selectivity $$\Sigma = \frac{(\% \; \text{isobutene}) \; \text{effluent} - (\% \; \text{isobutene}) \; \text{charge}}{\Sigma(\% \; n\text{-butenes}) \; \text{charge} - \Sigma(\% \; n\text{-butene effluent})} \times 100$$

The catalyst used in these examples is a commercial gamma alumina support impregnated with 0.1% titanium from decahydrated titanium oxalate in aqueous solution and then dried at 100° C. for 2 hours and calcined at 600° C. for 2 hours. The catalyst previously underwent a steam treatment at 560° C., for 20 hours and with a partial steam pressure of 0.8 bar. The hydrocarbon charge treated has the composition given in table 1.

TABLE 1

| Charge | wt. % |
|---|---|
| iC$_4$ | 0.216 |
| nC$_4$ | 21.76 |
| C$_4$=2TR | 2.732 |
| C$_{4=1}$ | 63.878 |
| iC$_4$= | 5.617 |
| C$_4$=2Cis | 5.139 |
| C$_4$== | 0.03 |
| C$_5$+ | 0.628 |

Use is made of a "radial" reactor as described in U.S. Pat. No. 4,277,444 in the name of the present applicant. The intake temperature is 530° C. and the volume space velocity is 2 liquid charge volumes at 15° C. per catalyst volume and per hour. The steam level injected is 2 mole per mole of C$_4$ fraction, which represents approximately 0.6 g/g of catalyst. The pressure on entering the reactor is 1.8 bar. The catalyst quantity is 55 m$^3$. The catalyst is replenished at a flow rate of 380 kg/h. The steam flow rate in the lift is 10 kg/h.

EXAMPLE 1

(comparative)

In this example the spent catalyst from the reactor (1) undergoes a regeneration by combustion of coke under the following conditions. The temperature on entering the regeneration zone (6) is maintained at 490° C., the pressure in the regenerator (6) at 2 bars, the oxygen content of the gaseous mixture (nitrogen plus air) introduced at 0.5 vol. % and the residence time in said zone 90 min. The regenerator is then purged with nitrogen and placed under a nitrogen atmosphere in pressure equilibrium with said reactor.

The catalyst is rapidly deactivated during cycles, so that there is a spectacular drop in the conversion and consequently a significant drop in the isobutene yield. The results obtained are given in table 2.

TABLE 2

| Operating hours (h) | Conversion $nC_4$ = (wt. %) | Selectivity $iC_4$ = (wt. %) | Yield $iC_4$ = (wt. %) |
| --- | --- | --- | --- |
| 250 | 31.2 | 83.5 | 26.0 |
| 1250 | 27.5 | 85.3 | 23.5 |
| 1350 | 26.5 | 86.8 | 23.0 |

EXAMPLE 2

(according to the invention)

A catalyst batch with the same formulation is used. The same apparatus and the same conditions as described relative to example 1 are used.

The regeneration protocol is identical except for the performance of a steam treatment phase in the regenerator (6) after combustion of coke. This is carried out at 530° C. under a steam pressure of 2 bars for 1 hour. The steam quantity in contact with the catalyst is 0.6 g/g of catalyst. The catalyst is then transported by the lift (11) under a steam atmosphere into the reactor (1).

Under these conditions the catalyst is very stable during the cycles, which leads to the maintaining of a high conversion level, a constant isobutene selectivity during the cycles and consequently a substantially constant isobutene yield over a period of time. The results obtained are given in table 3.

TABLE 3

| Operating hours (h) | Conversion $nC_4$ = (wt. %) | Selectivity $iC_4$ = (wt. %) | Yield $iC_4$ = (wt. %) |
| --- | --- | --- | --- |
| 250 | 33.7 | 83.1 | 28.0 |
| 1250 | 33.5 | 83.3 | 27.9 |
| 1350 | 33.6 | 82.8 | 27.8 |

The following meanings are used in the tables: $C_2$ ethane, $C_2$=: ethylene, $C_3$: propane, $iC_4$: isobutane, $nC_4$: n-butane, $C_4$=2TR:butene-2trans, $C_4$=1: butene-1, $iC_4$=: isobutene, $C_4$=2Cis: butene-2cis, $C_4$==: butadiene and $C_5$+: hydrocarbons with 5 or more carbon atoms.

EXAMPLE 3

(comparative with U.S. Pat. No. 3,558,733)

Example 3 differs from example 2 in that the catalyst used is commercial gamma alumina only, i.e. it is not impregnated with titanium. Prior to any contact with the charge, said catalyst undergoes a steam treatment at 560° C. for 20 hours and with a low partial steam pressure of 0.04 bar.

The hydrocarbon charge has the composition defined in table 1. The operating conditions are the same as those used in example 2, except that the vapour level injected is very low, being 0.2 mole/mole of $C_4$ fraction. The steam quantity in contact with the catalyst is then 0.06 g/g of catalyst.

All the other operations are identical to those described in example 2. The performance characteristics are given in table 4. The stability and selectivity of the catalyst are lower than those obtained with an alumina/titanium catalyst used with a high water/$C_4$ fraction molar ratio.

TABLE 4

| Operating hours (h) | Conversion $nC_4$ = (wt. %) | Selectivity $iC_4$ = (wt. %) | Yield $iC_4$ = (wt. %) |
| --- | --- | --- | --- |
| 250 | 44.2 | 60.5 | 26.75 |
| 1250 | 40.0 | 64.3 | 25.7 |
| 1350 | 37.5 | 66.2 | 24.8 |

In conclusion, example 1 clearly shows the need of the steam treatment after regeneration using an adequate water quantity and at a temperature close to that of the reaction zone.

Comparative example 3 clearly shows that with a prior art catalyst (U.S. Pat. No. 3,588,733) based on alumina, but not containing titanium and regenerated by calcination followed by vapour treatment, but with different water quantities, the performance characteristics obtained with regards to skeletal isomerization are well below those obtained by the process according to the invention.

Apart from the superior performance characteristics, the process also has the advantage of being simple to perform (no fluorine supply, as in the case of fluorine-containing catalysts), whilst being reliable from the apparatus standpoint (heat stresses minimized due to the fact that the temperature remains substantially constant throughout the stages of the process).

We claim:

1. A process for the skeletal isomerization of n-olefins containing at most 20 carbon atoms, comprising (a) contacting in a containing catalyst particles of a diameter of about 1–3 mm reaction zone and in the presence of water, a charge containing the n-olefins with an alumina-based catalyst containing alumina and 0.03 to 0.6 wt. % of titanium, at a water/olefin charge molar ratio between 0.1 and 3, a reaction zone temperature between 300° and 600° C., a pressure between 1 and 10 bars, and a space velocity of the charge between 0.1 and 10 $h^{-1}$, and wherein the process takes place continuously, (b) passing the catalyst through the reaction zone, (c) drawing the catalyst off for regeneration, (d) regenerating the catalyst and treating the catalyst with steam at a temperature substantially equal to that of the reaction zone, the steam quantity in contact with the catalyst in the reaction zone and during the treatment after regeneration being between 3 and 85 wt. % based on the catalyst weight, and (e) recontacting the catalyst with the charge.

2. A process according to claim 1, wherein the catalyst flow is under a steam atmosphere.

3. A process according to claim 1, wherein steam treatment is performed at between 110° and 700° C. under a partial steam pressure above 0.1 bar and for between 6 min and 10 hours.

4. A process according to claim 1, wherein catalyst is regenerated by injecting a gas containing oxygen, at a temperature of 350° to 550° C. and under a pressure between 1 and 15 bars.

5. A process according to claim 1, wherein flow in the reaction zone is radial.

6. A process according claim 1, wherein catalyst is periodically extracted from the reaction zone.

7. A process according to claim 1, wherein regeneration is performed batchwise.

8. A process according claim 1, wherein steam treatment is performed batchwise.

9. A process according to claim 1, wherein catalyst flow is continuous.

* * * * *